United States Patent [19]

Jordan et al.

[11] Patent Number: 5,102,631
[45] Date of Patent: Apr. 7, 1992

[54] EVAPORATION CHIMNEY

[75] Inventors: Willie W. Jordan, Garland; Thomas L. Clemmer, Euless, both of Tex.

[73] Assignee: Abbott Laboratories, Abbott Park, Ill.

[21] Appl. No.: 452,535

[22] Filed: Dec. 18, 1989

[51] Int. Cl.5 .......................... B01J 19/00; B01L 3/00
[52] U.S. Cl. .................................... 422/42; 422/99; 422/102; 206/814; 215/100 R; 220/528; 220/529
[58] Field of Search ............... 220/501, 506, 528, 529; 215/100 R; 206/814; 422/99, 102, 40, 41, 42, 43; 73/864.91

[56] References Cited

U.S. PATENT DOCUMENTS

| | | | |
|---|---|---|---|
| 3,788,815 | 1/1974 | Rohrbaugh | 23/253 |
| 3,942,660 | 3/1976 | Paller | 215/31 |
| 4,001,099 | 1/1977 | Wang et al. | 427/248.1 |
| 4,094,641 | 6/1978 | Friswell | 23/230 |
| 4,209,307 | 6/1980 | Leonard | 55/16 |
| 4,341,317 | 7/1982 | Suzuki et al. | 215/31 |
| 4,362,250 | 12/1982 | Cottingham | 215/247 |
| 4,426,003 | 1/1984 | Zarov | 422/42 |
| 4,458,584 | 7/1984 | Annese et al. | 99/323 |
| 4,483,616 | 11/1984 | Liston et al. | 356/246 |
| 4,578,588 | 3/1986 | Galkin | 250/432 |
| 4,696,411 | 9/1987 | Graf et al. | 422/99 |
| 4,789,639 | 12/1988 | Fleming | 422/102 |

Primary Examiner—Robert J. Warden
Assistant Examiner—Theresa A. Trembley
Attorney, Agent, or Firm—Roberta L. Hastreiter; Thomas M. Breininger

[57] ABSTRACT

An evaporation reduction apparatus for open mouth liquid containers and a method for substantially reducing liquid to air evaporation surface exposure wherein an elongated tube having an upper end portion of such outside dimension in relationship to the inside container mouth dimension to form a press fit upon insertion of the tube into the container. The tube having a bottom end and bottom end portion with at least one elongated slot open at the tube bottom end extending upwardly from the tube bottom, the tube having at least one bore passage in an upper end portion wall for fill venting purposes. The tube or evaporation chimney providing a method for reducing liquid evaporation from the open mouth container by reducing the actual liquid surface area exposed to ambient air.

17 Claims, 1 Drawing Sheet

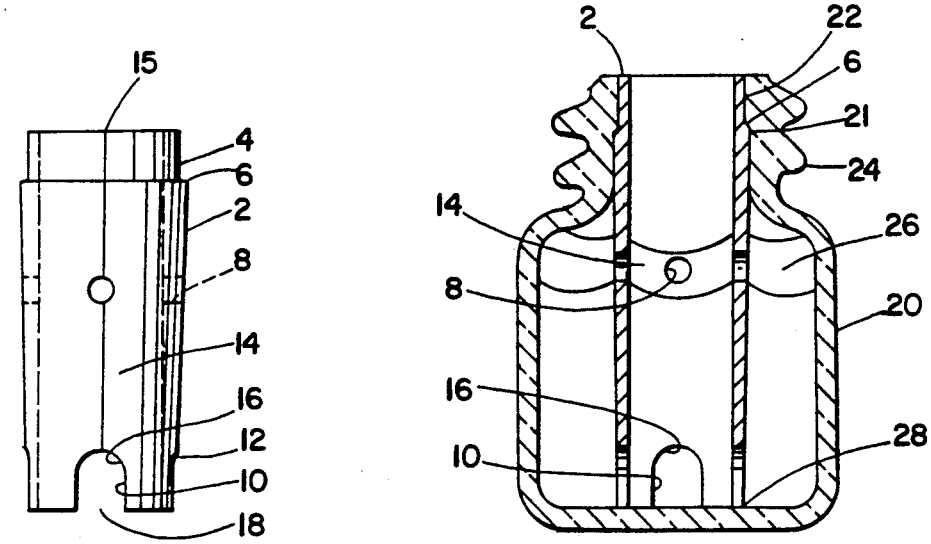
Fig. 1
Fig. 2
Fig. 4
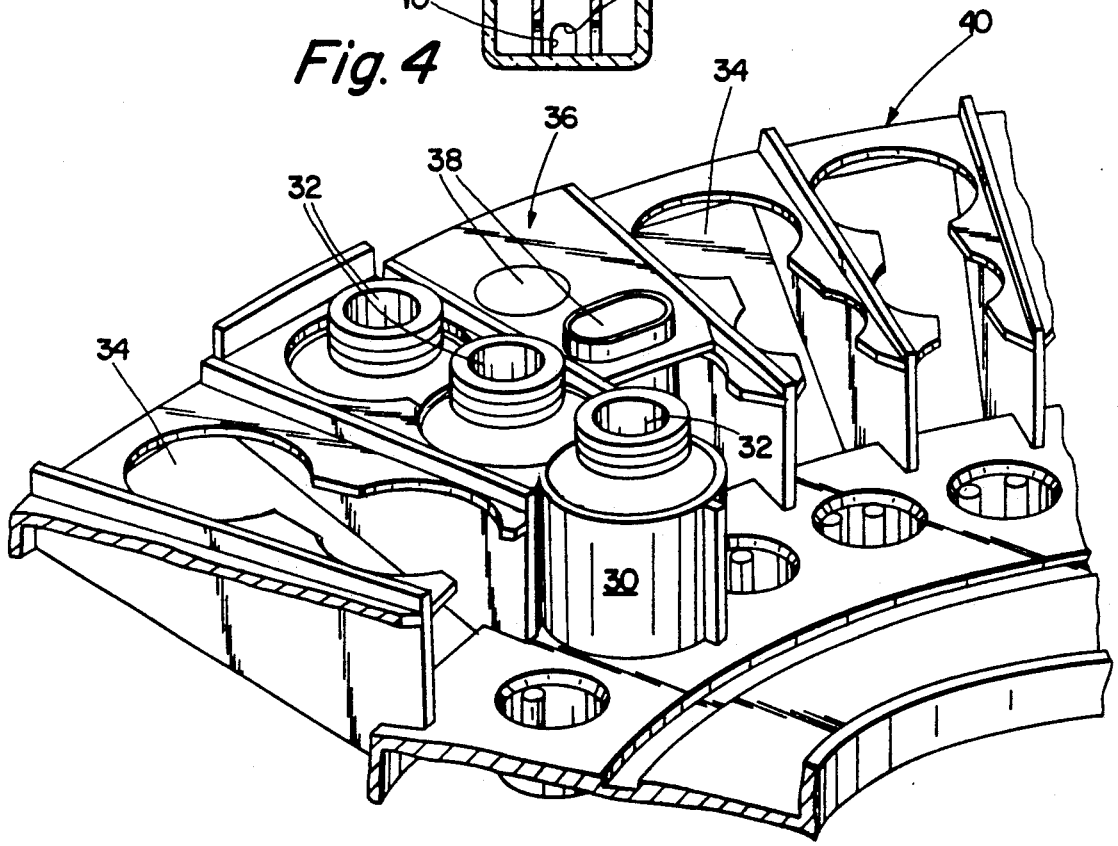
Fig. 3

EVAPORATION CHIMNEY

FIELD OF THE INVENTION

This invention relates to a chimney or vial insert comprised of a tube which fits tightly into the neck of a open mouth liquid container and extends down into the container or to the bottom thereby providing an evaporation reduction apparatus for the liquid containing open mouth container. The evaporation reduction apparatus according to the invention reduces the effective surface area of liquid exposed to air which is contained in the open mouth liquid container or vial. In yet another aspect, the chimney in reducing evaporation of liquid reagent materials can reduce potentially the open mouth container size requirement and when used in a diagnostic testing process for containing reagents, increase the number of tests per kit per reagent vial.

BACKGROUND OF THE INVENTION

In the field of diagnostic testing of biological fluids for the presence of drugs, viral disease, bacterial infections, and the like, samples are collected, reacted with reagents, and the results of the reactions analyzed using well known techniques. The reagents used in such tests are typically purchased in and drawn from vials or other containers which are often arranged for convenience in preformed packs having a plurality of such vials containing the reagents required for specific tests. For economy and practicality, each vial typically contains an aliquot of reagent sufficient to test a number of samples. A problem with such "multi dose" reagent packs is that once open, the reagents may become contaminated or concentrated through evaporation. For example, the properties of certain reagents may be effected by exposure to light or air, the passage of time, or exposure to other reagents or contaminents.

The vials of such packs could be individually reclosed using individual screw on or other closures typically provided with such vials. However, such individual closures can be misplaced or lost when separated from their respective vials. In addition, it is time consuming and inconvenient to individually open and reclose each vial with a separate closure, particularly in an automatic testing environment where test set up time and the time between tests can have a critical impact on through put.

Modern testing means require specific test protocal with specific reagents which are selected to identify for example, a particular analyte or analytes. The protocal specifies the sequence in which sample and reagents are to be introduced, the timing for the introduction of sample and reagents, the volumes of each to be used, and other conditions to be controlled such as temperature. The resulting mixture is typically allowed to incubate for a predetermined time and is then read, optically or otherwise, to determine the presence and concentration of the specific analyte which the assay is designed to identify.

Automated clinical analyzers are capable of performing imuno assays on an entire batch of samples simultaneously. In some types of known analyzers such as the well known TDx ® clinical analyzer manufactured by Abbott Laboratories of North Chicago, Ill., a batch of sample containers are mounted radially about a rotatable cassette together with a corresponding number of reagent containers. The carousel is then mounted inside the analyzer. Inside the analyzer, the carousel rotates stepwise to move each corresponding sample container and reaction container paired first to a position adjacent a preparation station, and then to a second position adjacent a reading station. A mechanical apparatus having pipeting means and typically operating under program control is located in proximity to the preparation station. Also located in proximity to the preparation station are a plurality of reagent containers which contain the reagents required to perform a specific assay on the batch of samples contained in the sample containers. The reagent containers may be individual containers or may be configured as an integrated pack.

At the preparation station, the mechanical apparatus and pipeting means operate to access and transfer volumes of sample from a sample container and reagents from the reagent containers into a reaction container according to the protocal established for the specific assay. When the mechanical apparatus completes the preparation of the reaction mixture according to the test protocal, the carousel rotates positioning the next corresponding sample container and reaction container pair adjacent the preparation station, and moving the previous pair toward the reading station. Known carousels typically hold twenty to twenty-five sample containers.

Through put limitations associated with the need and desire to test the same biological sample for more than one analyte such as when testing for the usage of a number of selected illegal drugs presents problems in that each test must be carried out sequentially. In the past, between tests, such analyzers were set up with new reagents and new samples being loaded and instructions for the new test located or entered. The requirement of changing reagent packs for each assay has an adverse impact on through put of the analyzer. Where multiple assays are to be performed on the same batch of samples or on different samples, the requirement of changing reagent containers for each assay has an even more severe and diversed impact on the though put of the system. Decreased through put increases both the time and cost associated with such assays.

Several approaches to solving the problems of through put of these analyzers have been provided, for example in providing unit dose for utilized reagent containers each containing an aliquot of reagents sufficient to carry out a specific assay on one sample. These containers are mounted on the analyzer carousel in positions corresponding to each sample container. With utilized reagent containers, different imuno assays can be carried out on each sample. For example, one sample can be assayed for a certain class of drugs, the next for the presence of a strain of virus, the next for a certain class bacteria, and so forth.

The unit dose approach has not provided a complete solution to the through put problems. However, multidose reagent pack and carousel for automated clinical analyzer have been adapted to hold such packs together with a plurality of conventional sample containers which contain samples to be assayed by the analyzer. For example, a reagent pack which includes a vial carrier having a plurality of vial receiving wells for containing a corresponding plurality of mutlidose reagent containing vials has been presented for automated clinical analyzer use. In addition, containment apparatus which is capable of holding a plurality of samples, the sample containers being adapted to be expeditiously mounted sequentially on carousels of a selected plurality of optimized clinical analyzers, the analyzers being networked to perform a selected battery of tests on each of the plurality of the samples has been proposed. All of these approaches are geared for increasing though put and performing multiple tests on samples using multiples of reagents, thus increasing the need for open reagent vials capable of delivering multiple doses of reagents at or near design concentrations as well as the avoidance of evaporation due to the requirement of continuously being open to air and pipeting.

The present invention has as a primary objective to satisfy the foregoing needs by providing a sample and reagent containment mechanism especially adapted for use in an automated analyzer network of the type described and having the foregoing and other features and advantages. Additional objectives are achieved by the evaporation chimney when utilized in any open mouth liquid containers wherein valuable liquids are maintained and which require immediate i.e., open access. In all of these situations the exposed liquids require maintenance of concentration and reduced evaporation into air or other environmental gases.

SUMMARY OF THE INVENTION

The invention satisfies the foregoing needs and achieves the foregoing features and advantages by providing an evaporation chimney for reagent containment apparatus comprised of an insertable tube which is inserted into the open mouth container or vial thereby providing a press tight fit, preferably airtight at the mouth and a reduced evaporation surface area.

The evaporation chimney or evaporation reduction apparatus for open mouth liquid containers of the present invention provides an apparatus and method for substantially reducing liquid to air evaporation surface exposure. The chimney comprising an elongated tube having an upper end portion of such dimension to afford an airtight press fit seal with the inside container mouth dimension is presented. The chimney having a substantially reduced inside dimension relative to the container extends downward into the container into the liquid level thereby presenting a reduced air to liquid evaporation surface. The evaporation chimney tube is further comprised of at least one slit in a bottom portion which allows circulation and equilibrium of concentration of the liquid. The tube is also provided with at least one upper end portion passage or bore opening above the normal liquid level which provides for venting during filling. The evaporation chimney according to the invention can be utilized with various shaped open mouth containers for example, those having reduced mouth dimensions as well as those having equal inside dimensions of mouth and body such as wide mouth containers and the like. In applications wherein the open mouth container is of the same dimension as that of the inside dimension of the container, the chimney has a large airtight press fitting for the mouth and reduced tube cross-sectional dimensions which are inserted into container and liquid levels. In general, the chimneys are inserted to a depth which optionally fit against the bottom of the container as a way of insuring the proper press fit of the airtight mouth connection. In any case, the chimney must afford sufficient passageway opening for utilization as, for example, reagent containers during automatic pipeting withdrawal. The need for open mouth containers for automatic carousels using reagent packs neccessitates the use of the evaporation chimney apparatus and method according to the invention. In known analyzer systems utilizing open mouth reagent containers, the reduction of evaporation not only provides for consistent concentration of reagents but also provides mechanism wherein the volume of reagent necessary for an exact number of assays can be reduced because of the efficient maintenance of the reagent volume.

BRIEF DESCRIPTION OF THE DRAWINGS

The features which are believed to define the invention are set forth in the appended claims. The invention itself, together with its features, objects, and attendant advantages, will be best understood by reference to the following detailed description of embodiments thereof, taken in conjunction with the accompanying drawings, in which:

FIG. 1 is a front elevated view of one form of the fluid container evaporation chimney;

FIG. 2 is a sectional view through an open mouth container with the evaporation chimney of FIG. 1 in place within the container;

FIG. 3 is a partial perspective view of an environment embodiment for the evaporation chimney in combination with a reagent pack containing open mouth reagent vials and sample containers mounted in a carousel utilized in automatic analyzers; and FIG. 4 is a sectional view through a wide mouth, open mouth container with a tapered evaporation chimney in place within the container.

DETAILED DESCRIPTION

As shown in FIGS. 1, 2, 3, and 4, embodiments of the present invention comprises the use of an evaporation chimney in cooperation with reagent vial and other open mouth containers. Reagent vial containers are utilized singly or in multiple dose reagent packs in corresponding carousel for automated analyzer systems. The reagent packs contain a plurality of vial receiving wells which receive and hold a plurality of reagent containing vials to form unitary packs. The carousel contains a plurality of radially spaced compartments which are adapted to receive and hold either a reagent pack or a sample container. A corresponding plurality of reaction container openings are provided on the carousel. The open mouth reagent vials contained in the reagent packs for specific assays are selectively interspersed with sample containers in the compartments to provide a wide variety of test combinations.

Referring to the drawings, FIG. 1 presents a front elevated view of the evaporation chimney 2 having an open end outside dimension 4 which press fits in a airtight fitting with the inside diameter of an open mouth container 20 as shown in FIG. 2. The seal ring 6 enhances the press fit upon insertion of the evaporation chimney 2 into the open mouth container 20. Fill vents 8 (for example, from about two to four openings) of the evaporation chimney 2 allow quick and efficient filling of the open mouth container 20 with liquid without splashback and other trapped air adverse reaction phenomena. In addition, the evaporation chimney 2 has fill opening slots 10 (for example, for about two to four slots) extending from the bottom of the evaporation chimney 2 from a slot open end 18 to various slot heights 16. The evaporation chimney 2 has a lower end portion chimney taper 12 which enhances ease of insertion of the press fitting evaporation chimney into the open mouth liquid container 20. A reduced cross-sectional area available for air to liquid evaporation is defined by area 14 which extends the length of the evaporation chimney 2 and is of the same cross-sectional area as the evaporation chimney 2 opening 15.

In FIG. 2, an open mouth container 20 having restricted mouth opening 22 and vial container threads 24 is illustrated with the evaporation chimney 2 inserted and in place in the open mouth container 20. Restricted mouth opening 22 fits the chimney open end outside dimension 4 which in combination with the seal ring 6 and expanded inside diameter of the vial container neck dimension 21 insures an airtight press fit. The open mouth container 20 and evaporation chimney 2 both interface with a liquid level 26 and define a reduced area for evaporation i.e., air to liquid interface equal to the surface area 14 of evaporation chimney 2. The evaporation chimney 2 is optionally insertable to rest on the bottom 28 of open mouth container 20. Such bottom to bottom connection of the evaporation chimney 2 and the open mouth container 20 is not necessary. However, such a dimensional relationship allows exact positioning of the evaporation chimney to the bottom of the open mouth container 20 and avoids inserting a shorter evaporation chimney 2 beyond its airtight fitting means as defined by seal ring 6.

The evaporation chimney 2 is generally of a cylindrical tube configuration or modified cylindrical tube which reduces evaporation by reducing effective surface area of the liquid reagent in the open mouth container 20 which is exposed to the air through the container's mouth opening. In addition to the preferred embodiments as shown in FIGS. 1 and 2, wide mouth open mouth containers having equal inside dimensions of the container and mouth i.e., no necked opening configurations, can be accomodated by modified evaporation chimney in accordance with the container and chimney as shown in FIG. 4. The wide mouth chimney 42 of FIG. 4 has a broad dimension at the top which forms an airtight press fit with the inside dimension of the open wide mouth 44 and yet, present a reduced effective surface area and reduced evaporation through a tapered or reduced diameter tubular chimney body 46 from the enlarged airtight fit dimension 48. For example, such an evaporation chimney has a greatly expanded upper portion which fits the large open wide mouth 44 container opening and a reduced elongated body 46 which actually forms reduced effective surface area at the liquid level 50 within the enlarged open mouth type of container. Even in the preferred embodiment as illustrated in FIGS. 1 and 2, a necked type open mouth container could be provided with an even more severely reduced effective surface area by further tapering of the elongated body portion which makes contact with the liquid inside the open mouth liquid container. Limitations of the actual reduced effective surface area of the air to liquid evaporation is somewhat dictated by the need for minimum dimensions i.e., diameter of the reduced surface area required by pipeting and filling operations.

In FIG. 3, a partial perspective view illustrates an environmental embodiment for the evaporation chimney in combination with a reagent pack and sample containers mounted in a carousel. A reagent pack 30 having three cylindrical vial receiving wells is presented wherein three open mouth reagent vials 32 are inserted. Wells 34 have a plurality of inwardly protruding vertical ribs radially spaced about the inner wall thereof, the ribs being adapted to provide a secure press fit with the outside surface of the open mouth reagent vials 32 when the vials 32 are mounted in wells 34. In addition, the carousel section 40 presents sample cups 36 in place next to the reagent pack 30. The sample cups 36 contain sample receiving wells 38.

The outer surface of the carousel provides a location for labeling means which preferably include both operator readable identifying information in the form of graphics or alpha numeric designations, for example, an analyzer readable information such as an optical bar code. The labeling means are advantageously used to identify to the operator and/or the analyzer the assay for which the reagent pack 30 is intended. Labeling means also provides convenient means for tracking a test sample through the entire analyst procedure with the analyzer instrument.

The open mouth reagent vials 32 are preferably formed at minimum cost of flexible plastic by conventional plastic molding techniques. Alternatively, glass or other vials can be used. The evaporation chimneys are also preferably formed of flexible plastic by conventional plastic molding techniques. Flexibility of the evaporation chimney enhances the press fitting of the chimney within the open mouth containers even if the container is constructed of more flexible glass or other rigid materials. The vials 32 are generally cylindrical in shape and have a vertical dimension sufficient to elevate the neck and opening of the vial 30 above the opening of wells 30 for ease of access when the vial 32 is mounted in the wells 34. In one embodiment, each open mouth reagent vial 32 preferably has the capacity of approximately 2.5 ml of a selected reagent, which is typically sufficient to perform assays on approximately 50 samples. Although it would be possible to form the open mouth container vials 32 integrally with the reagent pack 30 and/or vial carrier, it is preferred that the two components be embodied separately. Separate open mouth reagent vials 32 are easier to fill and avoid the risk of contaminating the reagent in one vial with the reagents from adjacent vials during the filling process. Also, in the preferred embodiment, both the open mouth reagent vials 32 and the reagent pack 30 are disposable as a single unit when the reagents in the vials 32 are expended.

We claim:

1. An evaporation reduction apparatus for open mouth liquid containers, comprising an elongated tube having an upper portion and an upper end portion, the upper end portion having an outside dimension approximately equal to the inside dimension of a mouth of an open mouth container, the upper end portion of the elongated tube and the mouth of the open mouth container forming an airtight fit upon insertion of the elongated tube into the open mouth container; the elongated tube having a bottom end and a bottom end portion with at least one elongated slot in the tube wall open at the tube bottom end extending upwardly from the bottom end, the tube elongated having at least one opening in the tube upper portion wall, the elongated tube inside diameter defining a liquid to air evaporation exposure area which is smaller than the evaporation exposure area of the open mouth container.

2. The evaporation reduction apparatus according to claim 1 wherein the elongated tube is constructed of flexible material so that upon insertion of the elongated tube, the tube upper end portion forms an airtight compression fit between the outside dimension of the elongated tube and the inside dimension of the mouth of the open mouth container.

3. The evaporation reduction apparatus according to claim 2 wherein the elongated tube extends to the bottom of the open mouth container affording controlled insertion and positioning for the airtight compression fit.

4. The evaporation reduction apparatus according to claim 1 wherein the elongated tube is cylindrical and is constructed with an inside diameter of equal dimension throughout the length of the elongated tube.

5. The evaporation reduction apparatus according to claim 1 wherein the open mouth container has a mouth inside dimension which is smaller than the inside dimension of the open mouth container and liquid level.

6. The evaporation reduction apparatus according to claim 1 wherein the liquid surface area which is exposed to ambient air is reduced to the liquid surface area inside the elongated tube which is reduced by 25% to 75%.

7. The evaporation reduction apparatus according to claim 1 wherein the elongated tube has from about two to about four openings and from about two to about four elongated slots in the tube walls.

8. The evaporation reduction apparatus according to claim 1 wherein the tube lower end portion outside dimension is tapered inwardly and is of a lesser dimension than the inside dimension of the open mouth container opening.

9. The evaporation reduction apparatus according to claim 5 wherein the tube upper end portion is inwardly tapered from the airtight mouth fit to a reduced internal dimension which extends from the end of the taper through the remaining part of the elongated tube to the bottom end of the elongated tube.

10. The evaporation reduction apparatus according to claim 1 wherein the mouth of the open mouth container has an inside diameter approximately equal to the inside diameter of the open mouth container and the elongated tube is tapered inwardly from the airtight mouth tube fit defining a reduced inside diameter which extends to the bottom of the elongated tube.

11. The evaporation reduction apparatus according to claim 1 wherein the upper end portion of the tube has a reduced outside diameter which is suitable for compression fitting against a neck ring positioned inside the mouth of the open mouth container.

12. An evaporation chimney for open mouth liquid containers, comprising an elongated chimney having an upper end portion with an outside dimension approximately equal to the inside dimension of a mouth of an open mouth container, the chimney upper end portion and the mouth of the open mouth container forming an airtight press fit upon insertion of the elongated chimney into the open mouth container; the elongated chimney having a bottom end and a bottom end portion with at least one elongated slot in the chimney wall open at the chimney bottom end extending upwardly from the bottom end, the chimney upper end portion having at least one wall opening, the elongated chimney inside dimension defining a liquid to air evaporation exposure area which is substantially smaller than the liquid evaporation exposed area of the open container.

13. A method for reducing evaporation of liquid contained in open mouth liquid containers comprising:
providing an open mouth container containing liquid;
inserting an evaporation chimney into the open mouth container and into the liquid contained in the open mouth container;
forming an airtight fit between the upper end portion of the chimney and the mouth of the container; thereby
reducing the surface area of liquid exposed to ambient air to the surface area defined by the liquid level inside the evaporation chimney.

14. The method for reducing evaporation of liquid contained in open mouth container according to claim 13 wherein the liquid evaporation surface exposure of ambiant air is reduced by at least 25%.

15. The method for reducing evaporation of liquid contained in open mouth containers according to claim 13 wherein the liquid is maintained in equilibrium concentration by communication of the liquid through slots in the lower end portion of the evaporation chimney between liquid chambers defined by the chimney inside liquid volume and the liquid volume outside the evaporation chimney.

16. The method for reducing evaporation of liquid contained in open mouth containers according to claim 13 wherein the evaporation chimney provides for rapid and uniform filling of the open mouth container with the evaporation chimney in place through filling bores in the chimney wall upper portion.

17. A method for maintaining concentration of liquid reagents contained in open mouth containers comprising:
providing an open mouth container containing liquid;
inserting an evaporation chimney into the open mouth container and into the liquid reagent in the open mouth container;
forming an airtight fit between the upper end portion of the chimney and the inside diameter of the mouth of the open mouth container thereby reducing the surface area of reagent liquid exposed to ambient gasses by at least 25%.

* * * * *

UNITED STATES PATENT AND TRADEMARK OFFICE
CERTIFICATE OF CORRECTION

PATENT NO. : 5,102,631
DATED : April 7, 1992
INVENTOR(S) : W. Jordan, T. Clemmer It is certified that error appears in the above-identified patent and that said Letters Patent is hereby corrected as shown below:

Column 5, line 68, delete "in wells" and insert --in the wells-- after "are mounted".
Column 8, line 22, delete "container" and insert --containers-- after "open mouth".

Signed and Sealed this

Thirty-first Day of August, 1993

Attest:

BRUCE LEHMAN

Attesting Officer          Commissioner of Patents and Trademarks